(12) United States Patent
Beachy et al.

(10) Patent No.: US 8,653,083 B2
(45) Date of Patent: Feb. 18, 2014

(54) HEDGEHOG PATHWAY ANTAGONISTS TO TREAT DISEASE

(75) Inventors: Philip A. Beachy, Stanford, CA (US); Jun O. Liu, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 596 days.

(21) Appl. No.: 11/990,729

(22) PCT Filed: Aug. 22, 2006

(86) PCT No.: PCT/US2006/032952
§ 371 (c)(1),
(2), (4) Date: Mar. 31, 2009

(87) PCT Pub. No.: WO2007/024971
PCT Pub. Date: Mar. 1, 2007

(65) Prior Publication Data
US 2009/0203713 A1    Aug. 13, 2009

Related U.S. Application Data

(60) Provisional application No. 60/710,117, filed on Aug. 22, 2005.

(51) Int. Cl.
*A61K 31/497*    (2006.01)
*A61K 31/415*    (2006.01)

(52) U.S. Cl.
USPC ..................... 514/254.07; 514/396

(58) Field of Classification Search
USPC ............................ 514/254.07, 396
See application file for complete search history.

(56) References Cited

U.S. PATENT DOCUMENTS

| | | | |
|---|---|---|---|
| 5,858,024 A | 1/1999 | De Lacharriere et al. | |
| 6,432,970 B2 | 8/2002 | Beachy et al. | |
| 6,552,016 B1 | 4/2003 | Baxter et al. | |
| 2002/0193384 A1 | 12/2002 | Fladung et al. | |
| 2005/0049207 A1* | 3/2005 | Kaufmann | 514/28 |

FOREIGN PATENT DOCUMENTS

| | | |
|---|---|---|
| EP | 0 171 628 A2 | 2/1986 |
| JP | H07-82162 A | 3/1995 |
| JP | H07-82163 A | 3/1995 |
| WO | WO 96/20709 A1 | 7/1996 |
| WO | WO 97/44014 A1 | 11/1997 |
| WO | WO 99/52534 A1 | 10/1999 |
| WO | WO 02/30462 A2 | 4/2002 |
| WO | WO 02/44344 A2 | 6/2002 |
| WO | WO 02/44344 A3 | 6/2002 |
| WO | WO 02/078704 A1 | 10/2002 |
| WO | WO 2004/105696 A2 | 12/2004 |
| WO | WO 2005/000208 A2 | 1/2005 |
| WO | WO 2006/004795 A2 | 1/2006 |

OTHER PUBLICATIONS

Ariyoshi et al., "Risk management in the proper use of the anticancer drug. The point for the proper use of the anticancer drug. The interaction between the drugs of the anticancer drug", *The Journal of Practical Pharmacy*, 55(3):1468-1480 (2004). English abstract and translation of section 5 on p. 1472 of the reference.

Kubo et al., "Hedgehog signaling pathway is a new therapeutic target for patients with breast cancer", *Cancer Res.*, 64(17):6071-4 (2004).

\* cited by examiner

*Primary Examiner* — Kevin E Weddington
(74) *Attorney, Agent, or Firm* — DLA Piper LLP (US)

(57) ABSTRACT

Compounds, compositions, kits and methods for modulating hedgehog pathway activity, and treating conditions related to abnormal or aberrant hedgehog pathway activity, are disclosed.

17 Claims, 1 Drawing Sheet

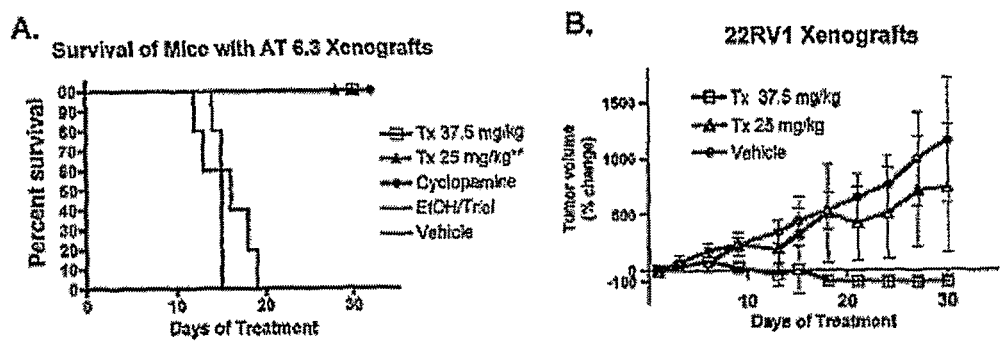

HEDGEHOG PATHWAY ANTAGONISTS TO TREAT DISEASE

CROSS-REFERENCE TO RELATED APPLICATION

This application claims the benefit of the following U.S. Provisional Application No. 60/710,117, filed Aug. 22, 2005, the entire disclosure of which is hereby incorporated in its entirety.

BACKGROUND OF THE INVENTION

The Hedgehog (Hh) signaling pathway is important in animal development, and has been highly conserved throughout evolution. Moreover, aberrant Hh signaling has been associated with the development and growth of many human cancers. As a result, the Hh signaling pathway has been a target in the research and development efforts of biotech and pharmaceutical companies to develop novel, non-toxic cancer treatments. Despite the massive scale of the resources dedicated to this approach, however, a Hh pathway antagonist that can be tested clinically for use in cancer therapy has not been achieved. Thus, there remains a need for the identification and development of drugs that act as Hh pathway antagonists.

First, identifying established drugs that also act as Hh pathway antagonists, and then using their already established toxicity profiles would facilitate the identification of Hh antagonists, and would more rapidly bridge the gap between the lab and the clinic. Thus, the present invention fills the need in the art for Hh pathway antagonists by providing identification of drugs with already established toxicity and pharmacokinetic profiles that can be used as compounds to inhibit Hh pathway activity, and treat a disorder or disease associated with aberrant Hh signaling, such as cancer.

SUMMARY OF THE INVENTION

The invention provides a method of inhibiting hedgehog pathway activity in a subject comprising administering an effective amount of a hedgehog antagonist, or a pharmaceutically acceptable salt thereof, to the subject, thereby inhibiting hedgehog pathway activity in the subject. The subject compounds of the invention may be formulated as a pharmaceutical preparation comprising a pharmaceutically acceptable excipient. The instant invention has therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Moreover, the subject methods can be performed on cells which are provided in culture (in vitro), or on cells in a whole animal (in vivo). See, for example, PCT publications WO 95/18856 and WO 96117924 (the specifications of which are expressly incorporated by reference herein). Other features and advantages of the invention will be apparent from the detailed description, and from the claims In one aspect, the invention provides a method of inhibiting hedgehog pathway activity in a subject. The method includes the step of administering an effective amount of a hedgehog antagonist selected from the compounds of Table 1, or a pharmaceutically acceptable salt thereof, to the subject, thereby inhibiting hedgehog pathway activity in the subject.

In certain embodiments, the hedgehog antagonist is selected from the group consisting of: itraconazole, sulfisomadine, podophyllum resin, colchicine, and colchiceine. In a presently preferred embodiment, the hedgehog antagonist is itraconazole. In certain embodiments, the subject is suffering from or susceptible to a disorder related to Hh pathway activity.

In another aspect, the invention provides a method of treating a disorder related to hedgehog pathway activity in a subject. The method includes the steps of (a) identifying a subject in need of treatment for a disorder related to Hh signaling; and (b) administering a compound selected from the compounds of Table 1, or a pharmaceutically acceptable salt thereof, to the subject, thereby treating a disorder related to hedgehog pathway activity in the subject.

In certain embodiments, the compound is itraconazole. In certain embodiments, the step of administering the compound includes administering the compound in a pharmaceutically acceptable composition. In certain embodiments, the method includes the further step of (c) monitoring the subject to determine the efficacy of treatment. In certain embodiments, the step of monitoring involves detecting a tumor size, and decrease in tumor size is indicative of treatment. In certain embodiments, the monitoring involves comparing the level of prostate specific antigen (PSA) in a serum sample after treatment to the level of prostate specific antigen before treatment. In certain embodiments, the disorder related to hedgehog pathway activity is cancer, psoriasis, or hirsutism. In certain embodiments, the disorder is cancer and the cancer is an endodermal carcinoma. In certain embodiments, the disorder is cancer and the cancer is selected from the group consisting of: prostate cancer, metastatic prostate cancer, small cell lung cancer, non-small cell lung cancer, carcinomas of the esophagus, stomach, pancreas, biliary tract, prostate, or bladder, basal cell carcinoma, medulloblastoma, rhabdomyosarcoma, breast cancer and ovarian cancer.

In another aspect, the invention provides a method of treating cancer in a subject in need of such treatment, the method comprising administering an effective amount of itraconazole, or a pharmaceutically acceptable salt thereof, to the subject, such that cancer is treated.

In certain embodiments, the cancer is selected from the group consisting of: prostate cancer, metastatic prostate cancer, small cell lung cancer, non-small cell lung cancer, carcinomas of the esophagus, stomach, pancreas, biliary tract, prostate, or bladder, basal cell carcinoma, medulloblastoma, rhabdomyosarcoma, breast cancer and ovarian cancer. In certain embodiments, the cancer is prostate cancer, and the prostate cancer is metastatic prostate cancer.

In another aspect, the invention provides a method for treating a disorder of aberrant hedgehog signaling in a subject suffering from or susceptible to a disorder of aberrant hedgehog signaling. The method includes the step of administering to the subject a therapeutically effective amount of itraconazole, or a pharmaceutically acceptable salt thereof, such that the disorder of aberrant hedgehog signaling is treated.

In another aspect, the invention provides a method for decreasing hedgehog pathway activity in a subject, comprising administering to a subject in need of such treatment an effective amount of a hedgehog antagonist selected from the compounds of Table 1, or a pharmaceutically acceptable salt thereof. In certain embodiments, the hedgehog antagonist is itraconazole.

In another embodiment, the invention provides a method for decreasing hedgehog pathway activity in a subject. The method includes the step of administering to a subject in need of such treatment an effective amount of a hedgehog antagonist selected from the compounds of Table 1, or a pharmaceutically acceptable salt thereof, in combination with a second form of therapy. In certain embodiments, the hedgehog antagonist is itraconazole. In certain embodiments, the second form of therapy is selected from the group consisting of: anti-androgen therapy, radiation therapy, surgical intervention, or antineoplastic chemotherapy.

In another aspect, the invention provides a method of treating prostate cancer in a subject. The method includes the step of administering an effective amount of itraconazole, or a pharmaceutically acceptable salt thereof, to the subject, thereby treating prostate cancer in the subject.

In certain embodiments, the prostate cancer is metastatic prostate cancer

In another aspect, the invention provides a method of treating a condition associated with hedgehog pathway activity in a subject. The method includes the step of administering to the subject effective amount of a hedgehog antagonist selected from the compounds listed on Table 1, such that the condition associated with hedgehog pathway activity is treated.

In certain embodiments, the condition associated with hedgehog pathway activity is not cancer.

In certain embodiments of the above aspects, the subject is a mammal. In certain embodiments, the subject is a human.

In certain embodiments of the above aspects, the effective amount of a hedgehog antagonist selected from the compounds of Table 1 is administered to the subject at a range of 0.0001 to about 100 mg per kilogram of body weight per day. In certain embodiments, the compound is administered to the subject by the method selected from the group consisting of: oral, topical, parenteral, and systemic.

In another aspect, the invention provides a method of inhibiting hedgehog signaling activity in a cell. The method includes the step of contacting the cell with (e.g., administering to the cell) an effective amount of any one of the compounds in Table 1, or a pharmaceutically acceptable salt thereof, thereby inhibiting hedgehog signaling activity in the cell.

In certain embodiments, the cell is not a neoplastic cell.

In another aspect, the invention provides a method of inhibiting hedgehog pathway activity in a cell. The method includes the step of administering an effective amount of a compound selected from the compounds of Table 1, or a pharmaceutically acceptable salt thereof, to the cell (contacting the cell with the compound), thereby inhibiting hedgehog pathway activity in the cell.

In certain embodiments of the above aspects, the cell is a mammalian cell, more preferably a human cell.

In yet another aspect, the invention provides a kit. The kit includes a hedgehog antagonist compound selected from the compounds of Table 1 in unit dosage form, together with instructions for using the compound for treating a condition related to hedgehog pathway activity.

Definitions

The term "aberrant signaling" is intended to refer to abnormal receptor activity in a cell, relative to receptor activity in a normal cell under similar conditions. For example, abnormal activity can be excessive or undesired levels of Hedgehog pathway activity in a cell, for example a malignant cell, compared to a non-malignant cell.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "prostate carcinoma", which refers to carcinomas arising from adenocarcinomas developing in the acini of prostatic ducts and has a high metastatic potential; "metastatic prostate carcinoma", which refers to a prostate carcinoma that has spread, either contiguously or via lymphatics, blood vessels, or the vertebral venous system, to tissues outside the prostate, e.g., the bones, liver, and/or lungs; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

By the term "decrease" is meant inhibit, suppress, attenuate, diminish, arrest, or stabilize Hh pathway activity.

By "disorder of Hh signaling" is meant a disorder associated with excessive or undesired levels of Hedgehog pathway activity, e.g. aberrant Hh signaling activity. In certain embodiments, the disorder of aberrant Hh pathway activity is a disorder of hyperproliferation, e.g., cancer or psoriasis. In other embodiments, the disorder of aberrant Hh activity signaling is not cancer.

The phrase "Hedgehog activity assay" is meant to refer to an in vitro or in vivo assay for determining the ability of a test compound to modulate (e.g., inhibit) hedgehog pathway activity.

The term "hedgehog antagonist" is meant to refer to an agent that will reduce the activity of smoothened, and reduce the activity of Hh pathway targets, patched and Gli1. When the Hh pathway is active, transcription of target genes is higher, when the Hh pathway is inactive, transcription of target genes is lower. Preferred hedgehog antagonists can be used to overcome a ptc loss-of-function and/or a smoothened gain-of-function, the latter also being referred to as smoothened antagonists. The term "hedgehog antagonist" as used herein refers not only to any agent that may act by directly inhibiting the normal function of the hedgehog protein, but also to any agent that inhibits hedgehog pathway activity, and thus recapitulates the function of ptc.

The phrase "hedgehog pathway activity" as used herein refers to activity of a signaling pathway that is activated by the hedgehog polypeptide (Hh) or the N-terminal fragment of Hh polypeptide (Hh-N) which is approximately 19 kD. The Hh polypeptide or the Hh-N polypeptide may be derived from a number of species including, without limitation, *Drosophila*, Zebrafish, *Xenopus*, chicken, murine or human. The Hh polypeptide may be, for example, the Sonic hedgehog polypeptide (Shh), Indian hedgehog polypeptide (Ihh), Desert hedgehog (Dhh) or their amino-terminal fragments, Shh-N, Ihh-N, and Dhh-N, respectively (see Porter et al., Nature 374:363, 1995; Porter et al., Science 274:255, 1996, herein incorporated by reference). Accordingly, the Hh-mediated signaling pathway may be the Shh-mediated signaling pathway, Ihh-mediated signaling pathway, Dhh-mediated signaling pathway, Shh-N-mediated signaling pathway, Ihh-N mediated signaling pathway, or Dhh-N-mediated signaling pathway. The endogenously produced HhN is predominantly found in dually lipid-modified form, with covalently attached palmitate and choleteryl moieties at the N- and C-termini respectively (Mann and Beachy, Ann Review Biochem. 2004). The Hh-mediated signaling pathway can include one or more molecules such as polypeptides and/or nucleic acids. The molecules in the signaling pathway may be altered in a number of ways in response to Hh polypeptide. For example, molecules may be phosphorylated or dephosphorylated. Molecules may also undergo conformational changes and/or bind to other molecules. Thus, a variety of signals may be generated due to the presence of the Hh polypeptide. Polypeptides involved in the Hh-mediated signaling pathway may include, without limitation, kinases, phosphatases, and polypeptides that interact with nucleic acid sequences (e.g., transcription factors). Nucleic acid molecules involved in the Hh-mediated signaling pathway may include, for example, polypeptide binding nucleic acid molecules. The hedgehog signaling pathway may be any species of hedgehog signaling pathway, including the *Drosophila*, Zebrafish, *Xenopus*, chicken, murine or human hedgehog signaling pathway. The hedgehog signaling pathway may be a vertebrate hedgehog signaling pathway, and more specifically, a human hedgehog signaling pathway. Transcription factors associated with the hedgehog signaling are described in U.S. Pat. No. 6,733,971, which is incorporated herein by reference.

The term "inhibit" or "inhibits" means to decrease, suppress, attenuate, diminish, arrest, or stabilize the development or progression of a disease or disorder, or the activity of a biological pathway, e.g., by at least 10, 20, 30, 40, 50, 60, 70, 80, 90, 95, 98, or 99% compared to an untreated control subject, cell, or biological pathway.

The term "$IC_{50}$" means the dose of a drug which is half the maximal inhibitory concentration.

The term "neoplasia" is meant any disease that is caused by or results in inappropriately high levels of cell division, inappropriately low levels of apoptosis, or both. For example, cancer is an example of a neoplasia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

The term "subject" refers to human or non-human animals, typically mammalian animals, such as primates (humans, apes, gibbons, chimpanzees, orangutans, macaques), domestic animals (dogs and cats), farm animals (horses, cattle, goats, sheep, pigs) and experimental animals (mouse, rat, rabbit, guinea pig). Subjects include animal disease models (e.g., tumor bearing mice).

The phrases "parenteral administration" and "administered parenterally" as used herein means modes of administration other than enteral and topical administration, usually by injection, and includes, without limitation, intravenous, intramuscular, intarterial, intrathecal, intracapsular, intraorbital, intracardiac, intradermal, intraperitoneal, transtracheal, subcutaneous, subcuticular, inimarticulare, subcapsular, subarachnoid, intraspinal and intrasternal injection and infusion.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

The term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "therapeutically effective amount" refers to an amount sufficient to produce the desired effect, e.g., to reduce or ameliorate the severity, duration, progression, or onset of a disease, condition, or disorder (e.g., a disease, condition, or disorder related to hedgehog pathway activity), or one or more symptoms thereof; prevent the advancement of a disease, condition, or disorder; cause the regression of a disease, condition, or disorder; prevent the recurrence, development, onset or progression of a symptom associated with a disease, condition, or disorder; or enhance or improve the prophylactic or therapeutic effect(s) of another therapy. An effective amount of a compound according to this invention can range from, e.g., about 0.001 mg/Kg to about 1000 mg/Kg, or about 0.1 mg/kg to about 100 mg/kg. Effective doses will also vary, as recognized by those skilled in the art, depending on the disorder treated, route of administration, excipient usage, the age and sex of the subject, and the possibility of co-usage with other therapeutic treatments such as use of other agents. It will be appreciated that an amount of a compound required for achieving, e.g., hedgehog antagonist activity, may be different from the amount of compound effective for another purpose (e.g., antifungal activity).

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "treatment" is intended to encompass also prophylaxis, therapy and cure.

As used herein, "transformed cell(s)" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

BRIEF DESCRIPTION OF THE DRAWINGS

FIG. 1 (A & B) is two graphs showing itraconazole treatment in prostate cancer models. A) Daily itraconazole treatment at two doses (T×37.5 and T×25 mg/kg) prolongs survival as effectively as cyclopamine in the AT6.3 metastasis model. B) Itraconazole treatment of established tumors from 22RV i human cancer cells in athymic mice slows growth (T×25 mg/kg) or causes complete regression (-100% volume; 37.5 mg/kg).

DETAILED DESCRIPTION OF THE INVENTION

The present invention relates to the discovery that signal transduction pathways regulated by hedgehog (Hh), patched (ptc), or smoothened (smo) can be inhibited by selected compounds, including itraconazole. While not wishing to be bound by any particular theory, these agents act by inhibiting Hh signaling activity, for example, by interfering with the ability of hedgehog (Hh), patched (ptc), and/or smoothened (smo) to activate a hedgehog, ptc, and/or smoothened-mediated signal transduction pathway.

Hedgehog (Hh)

The hedgehog (Hh) gene was initially identified based on its requirement for normal segmental patterning in *Drosophila* (Nusslein-Volhard, C. and Wieschaus, E., Nature 287: 795 801, 1980). Its functions include local signaling to coordinate the identities of adjacent cells within early embryonic segments (Hooper, J. E., and Scott, M. P. Early Embryonic Development of Animals, pp. 1-48, 1992) and a later function in cuticle patterning that extends across many cell diameters (Heernskerk, J. and DiNardo, S., Cell, 76:449 460, 1994). The Hh gene also functions in the patterning of imaginal precursors of adult structures, including the appendages and the eye (Mohler, J. Genetics, 120:1061 1072, 1988; Ma, et al., Cell, 75:927 938, 1993; Heberlein, et al., Cell, 75:913 926, 1993; Tabata, T. & Kornberg, T. D., Cell, 76:89 102, 1992; Basler, K. & Struhl, G., Nature, 368:208 214, 1994). Genetic and molecular evidence indicates that hedgehog proteins are secreted and function in extracellular signaling (Mohler, J., supra; Lee, et al., Cell, 71:33 50, 1992; Taylor, et al., Mech. Dev., 42:89 96, 1993).

In vertebrates, activities encoded by Hh homologues have been implicated in anterior/posterior patterning of the limb (Riddle, et al., Cell, 75:1401 1416, 1993; Chang, et al., Development, 120:3339, 1994), and in dorsal/ventral patterning of the neural tube (Echelard, et al., Cell, 75:1417 1430, 1993; Krauss, et al., Cell, 75:1431 1444, 1993; Roelink, et al., Cell, 76:761 775, 1994).

In most of the embryonic tissues where Hedgehog signaling exerts a patterning effect, activation of the Hedgehog pathway is associated with a proliferative response in target cells. Such embryonic tissues include but are not limited to the developing neural tube, the presomitic mesoderm and the mesoderm of the developing limb bud. In addition, uncontrolled cell proliferation due to inappropriate activation of the Hedgehog signaling pathway is associated with formation of several tumor types including but not limited to basal cell carcinoma, endodermal tumors, including prostate cancer, metastatic prostate cancer, small cell lung cancer, non-small cell lung cancer, carcinomas of the esophagus, stomach, pancreas, biliary tract, prostate, or bladder, basal cell carcinoma, medulloblastoma, rhabdomyosarcoma, breast cancer and ovarian cancer, medulloblastoma, and hematopoietic disorders, including leukemia and multiple myeloma.

The uncontrolled proliferation in these tumors is probably due to the abnormal activation of transcription factors such as Gli1 that have a normal role in the Hedgehog signaling pathway. For example, in the case of basal cell carcinoma, all or nearly all cases are associated with inappropriately high level expression of the Gli1 transcription factor in basal keratinocytes (Dahmane et al., Nature 1997, 389(6653): 876-881). Such inappropriate activation of Gli1 is thought to play a causal role in uncontrolled cell proliferation associated with basal cell carcinoma. The ability to modulate Hh pathway activity thus represents a possible therapeutic approach to several clinically significant cancers.

The hedgehog polypeptide (Hh) is synthesized as a precursor that undergoes autoprocessing to generate an amino-terminal fragment (Hh-N) and a carboxy-terminus fragment (Hh-C). Lee et al. Science, 266:1528 37, 1994. Hh-N contains all the signaling activities of Hh, whereas Hh-C is responsible for the autoprocessing and attaches a cholesterol molecule to the carboxy-terminal of h-N to regulate its spatial distribution. (Porter, J. A., et. al. Nature, 374:363 366, 1995. Porter, J. A., et. al. Science, 274:255 259, 1996. Porter, J. A. et. al. Cell, 86:21 34, 1996).

Dysregulation of a number of genes in the Hh signaling pathway can lead to a phenotype resembling Hh activation. Hedgehog gain-of-function refers to an aberrant modification or mutation of a ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the ptc gene product to regulate the level of expression of Ci genes, e.g., Gli1, Gli2, and Gli3. The term "hedgehog gain-of-function" can also refer to a similar cellular phenotype (e.g., exhibiting excess proliferation) which occurs due to an alteration anywhere in the hedgehog signal transduction pathway, including, but not limited to, a modification or mutation of hedgehog itself. For example, a tumor cell with an abnormally high proliferation rate due to activation of hedgehog pathway activity would have a "hedgehog gain-of-function" phenotype, even if hedgehog is not mutated in that cell.

Smoothened gain-of-function refers to an aberrant modification or mutation of a smo gene, or an increased level of expression of the gene, which results in a phenotype which resembles contacting a cell with a hedgehog protein, e.g., aberrant activation of a hedgehog pathway. While not wishing to be bound by any particular theory, it is noted that ptc may not signal directly into the cell, but rather interact with smoothened, another membrane-bound protein located downstream of ptc in hedgehog signaling (Marigo et al., (1996) Nature 384: 177-179). The gene smo is a segment-polarity gene required for the correct patterning of every segment in Drosophila (Alcedo et al., (1996) Cell 86: 221-232). Human homologs of smo have been identified. See, for example, Stone et al. (1996) Nature 384:129-134, and GenBank accession U84401. The smoothened gene encodes an integral membrane protein with characteristics of heterotrimeric G-protein-coupled receptors; i.e., 7-transmembrane regions. This protein shows homology to the Drosophila Frizzled (Fz) protein, a member of the wingless pathway. It was originally thought that smo encodes a receptor of the Hh signal. However, this suggestion was subsequently disproved, as evidence for ptc being the Hh receptor was obtained. Cells that express Smo fail to bind Hh, indicating that smo does not interact directly with Hh (Nusse, (1996) Nature 384: 119-120). Rather, the binding of Sonic hedgehog (SHH) to its receptor, PTCH, is thought to prevent normal inhibition by PTCH of smoothened (SMO), a seven-span transmembrane protein. U.S. Pat. No. 6,867,216, incorporated by reference herein in its entirety, teaches methods and reagents for inhibiting smoothened-dependent pathway activation. Patched loss-of-function refers to an aberrant modification or mutation of a ptc gene, or a decreased level of expression of the gene, which results in a phenotype which resembles contacting a cell with a hedgehog protein, e.g., aberrant activation of a hedgehog pathway. The term "ptc loss-of-function" is also used herein to refer to any similar cellular phenotype (e.g., exhibiting excess proliferation) which occurs due to an alteration anywhere in the hedgehog signal transduction pathway, including, but not limited to, a modification or mutation of ptc itself For example, a tumor cell with an abnormally high proliferation rate due to activation of hedgehog pathway activity would have a "ptc loss-of-function" phenotype, even if ptc is not mutated in that cell.

The Hh signaling pathway is best known for its role in directing pattern formation during embryonic development, but also functions post-embryonically in the activation and expansion of stem or progenitor cells in various adult tissues, particularly in response to tissue injury. This stem cell regulatory role of Hh signaling is of great potential relevance to cancer, which increasingly is viewed as a stem cell disease, both in its propagation by a minority of cells with stem-cell like properties and in its possible derivation from normal tissue stem cells U.S. Pat. No. 6,432,970, incorporated by reference herein in its entirety, describes assays and reagents for inhibiting paracrine and/or autocrine signals produced by a hedgehog protein comprising contacting a cell sensitive to the hedgehog protein with a steroidal alkaloid, or other small molecule, in a sufficient amount to reduce the sensitivity of the cell to the hedgehog protein.

Itraconazole

Itraconazole or (±)-cis-4-[4-[4-[4-[[2-(2,4-dichlorophenyl)-2-(1H-1,2,4-triazol-1-yl-methyl)-1,3-dioxolan-4-yl) methoxy]phenyl]-1-piperazinyl]phenyl]-2,4-dihydro-2-(1-methylpropyl)-3H-1,2,4-triazol-3-one, or alternatively 2-butan-2-yl-4-[4-[4-[4-[[(2R,4S)-2-(2,4-dichlorophenyl)-2-(1,2,4-triazol-1-ylmethyl)-1,3-dioxolan-4-yl]methoxy] phenyl]piperazin-1-yl]phenyl]-1,2,4-triazol-3-one, is a broad spectrum antifungal compound developed for oral, parenteral and topical use and is disclosed in U.S. Pat. No. 4,267,179, incorporated herein by reference in its entirety. A difluoro analog, saperconazole or (±-)-cis-4-[4-[4-[4-[[2-(2,4-difluorophenyl)-1H-1,2,4-triazol-1-ylmethyl-1)-1,3-dioxolan-4-yl]methoxy]phenyl]-1-piperazinyl]phenyl]-2,4-dihydro-2-(-1-methoxypropyl)-3H-1,2,4-triazol-3-one, has improved activity against Aspergillus spp. and is disclosed in U.S. Pat. No. 4,916,134, incorporated herein by reference in its entirety. Both itraconazole and saperconazole consist of a mixture of four diastereoisomers, the preparation and utility of which is disclosed in WO 93/19061: the diastereoisomers of itraconazole and saperconazole are designated [2R-[2.alpha., 4-alpha.,4(R*)]], [2R-[2.alpha.,4.alpha.,4(S*)]], [2S-[2.alpha.,4.alpha,4(S*)]] and [2S-(2.alpha.,4.alpha.,4(R*)]]. The term "itraconazole" as used hereinafter is to be interpreted broadly and comprises the free base form and the pharmaceutically acceptable addition salts of itraconazole, or of one of its stereoisomers, or of a mixture of two or three or four of its stereoisomers. The preferred itraconazole compound is the (±)-(2R*, 4S*) or (cis) forms of the free base form, having the Chemical Abstracts Registry Number [84625-61-6]. The acid addition forms may be obtained by reaction of the base form with an appropriate acid. Appropriate acids comprise, for example, inorganic acids such as hydrohalic acids, e.g. hydrochloric or hydrobromic acid; sulfuric acid; nitric acid; phosphoric acid and the like; or organic acids such as, for example, acetic, propanoic, hydroxyacetic, 2-hydroxypropanoic, 2-oxopropanoic, ethanedioic, propanedioic, butanedioic, (Z)-butenedioic, (E)-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Itraconazole is an FDA-approved drug that has now been found to have hedgehog-inhibitory activity (as measured in an in vitro assay) and has show clear efficacy in mouse models of prostate cancer (e.g., as shown in the Examples, infra), with an ability to suppress metastasis and cancer growth. Without wishing to be bound by any theory, it is believed that the hedgehog-inhibitory activity of itraconazole may be related (at least in part) to the ability of itraconazole to inhibit sterol biosynthesis, thereby inhibiting smoothened. For instance, one role for cholesterol is as a covalent adduct for the biologically active form of the hedgehog protein (Hh), which is formed as a product of an autoprocessing reaction that entails internal cleavage. Cholesterol attachment restricts the spatial deployment of the Hh signal, thus influencing the pattern of cellular responses in developing tissues. A review of cholesterol modification of Hh proteins is presented in Mann and Beachy (Ann. Rev. Biochem., Vol. 73: 891-923 (2004)) and incorporated herein by reference in its entirety. In addition to its role in Hh signal production, cholesterol has an essential role in mediating the response to the Hh signal within target cells, and this role is revealed by genetic or drug-induced perturbations of cholesterol homeostasis that render target tissues unresponsive to the Hh signal. As such, a defective response to hedgehog signaling is seen in certain disorders of cholesterol biosynthesis, such as desmosterolosis and lathosterolosis, human syndromes caused by defects in the final stages of cholesterol biosynthesis.

Screening Assays

The invention also relates to screening assays for identifying agents that antagonize Hedgehog (Hg) signaling. The screening method is also useful for identifying variants, binding or blocking agents, etc., which functionally, if not physically (e.g., sterically) act as antagonists or agonists, as desired.

Pharmaceutical Compositions

Pharmaceutical compositions and formulations of the present invention include pharmaceutical compositions of the Hedgehog antagonist compounds disclosed herein (e.g., the compounds of Table 1, such as itraconazole), that can be administered to a mammal, and can also include veterinary compositions, e.g., pharmaceutical preparations of the subject compounds suitable for veterinary uses, e.g., for the treatment of live stock or domestic animals, e.g., dogs. As described in further detail below, it is contemplated that the subject methods can be carried out using a variety of different Hedgehog antagonists, which can be readily identified by their $IC_{50}$ values. Exemplary Hedgehog antagonists for use in the subject methods include itraconazole and the compounds of Table 1, as follows: salinomycin sodium, oligomycin, colchicine, Podophyllum resin, Croton oil, Ipecac syrup, vindesine, vincristine sulfate, demecolcine, vinorelbine tartrate, loxapine succinate, cyproheptadine, itraconazole, colchiceine, pimethixene maeate, diaziquone, sulfisomidine, cyclohexamide, cyclopamine, cod liver oil, methoxyvone, promethazine hydrochloride, sulfaquinoxaline sodium, vinblastine sulfate, hydroxyzine, eucalyptol, rotenone, phenoxybenzamine hydrochloride, 5-azacytidine, W-7 hydrochloride, dihydroartemisinin, clompramine, raloxifine hydrochloride, doxazosin mesylate salt, dihydroartemisinin, Comipramine, Raloxafine hydrochloride, Doxazpsin mesylate salt, Chloroquine diphosphate salt, Imipramine, Thioridiazine, Clothiapine, Zolantidine, Crassin Acetate, Estriol Benzyl Ether, Fluphenazine N-mustard (SKF-7171A), Almond oil, Promazine Hydrochloride, Estradiol acetate, Trimipramine Maleate, Copper (II) acetate, Estradiol 3-benzoate, Amitriptyline, Chlorquinaldol (5,7-Dichloro-2-methyl-8-quinolinol).

In one embodiment, the methods and compositions of the present invention make use of itraconazole and pharmaceutically acceptable salts thereof. Other compounds useful in the methods and compositions of the invention include sulfisomidine (known as an antibiotic), and pharmaceutically acceptable salts thereof; podophyllum resin (known as a wart or corn treatment), and pharmaceutically acceptable salts thereof; and colchicine (known as a microtubule inhibitor in cancer therapy), and pharmaceutically acceptable salts thereof.

U.S. Pat. No. 6,485,743 describes oral preparations of itraconazole. U.S. Pat. No. 7,081,255 describes pharmaceutical compositions of itraconazole that can be administered to a mammal, whereby a single such dosage form can be administered once daily, and in addition at any time of the day independently of the food taken in by said mammal, and is herein incorporated by reference in its entirety. U.S. Pat. No. 6,946,137 provides a method for the controlled delivery of pharmacologically active compounds, such as itraconazole, over time, and is herein incorporated by reference in its entirety. U.S. Pat. No. 6,407,079 (incorporated herein by reference) describes pharmaceutical compositions in which cyclodextrin derivatives are used to solubilize compounds, including itraconazole, which are otherwise insoluble or only sparingly soluble in water.

The invention provides for compositions comprising a compound according to the invention, for example itraconazole, admixed with a physiologically compatible carrier. As used herein, "physiologically compatible carrier" refers to a physiologically acceptable diluents such as water, phosphate buffered saline, or saline, and further may include an adjuvant. Adjuvants such as incomplete Freund's adjuvant, aluminum phosphate, aluminum hydroxide, or alum are materials well known in the art.

Methods of introduction may be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a subject compound at a particular target site.

The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. For example, sulfisomidine in certain embodiments is administered in topical formulation, but can also be administered systemically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the subject. U.S. Pat. No. 6,737,082 describes pharmaceutical oral preparation of itraconazole compositions, and is herein incorporated by reference in its entirety.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Additional ingredients may be added to the topical composition, as long as they are pharmaceutically acceptable and not deleterious to the epithelial cells or their function. Further, they should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like may be present. The pH of the topical composition of this invention may be adjusted to a physiologically acceptable range of from about 6.0 to about 9.0 by adding buffering agents thereto in order for the composition to be physiologically compatible with the skin. In one embodiment, podophyllum resin is particularly suited for topical formulation for treating, for example cancerous lesions on the skin.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. . . . Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition with information including amount, frequency and method of administration.

The invention also includes the use of a compound in the manufacture of a medicament for inhibiting hedgehog pathway activity, wherein the compound is selected from the compounds listed in Table 1.

Combination Therapy

In certain embodiments, the invention contemplated combination therapies. For example, itraconazole can be used in therapy in combination with other compounds. For example, itraconazole can be co-administered in combination with other compounds, for example, at a ratio in the range of 1:1-1:5-5:1, 1:1-1:10-10:1, 1:1-1:25-25:1, 1:1-1:100-100:1, 1:1-1:1000-1000:1 or 1:1-1:10,000-10,000:1. Compounds contemplated for use in combination therapy with itraconazole include anti-androgens (including flutamide, bicalutamide, and nilutamide), LHRH agonists, luteinizing hormone releasing hormone (LHRH) antagonists, and chemotherapeutic agents such as gemcitabine particularly in pancreatic cancer treatment), platinum compounds (such as cis-platin, used in lung cancer treatment), mitozantrone, doxorubicin, vinblastine, paclitaxel, docetaxel, estramustine phosphate, and etoposide. Other combination therapy contemplated by the invention includes treatment with itraconazole in combination with surgery, e.g., surgical removal of a tumor and/or surrounding tissue, e.g., debulking of tumor mass. In one particular example, the combination therapy can be used in the treatment of medulloblastoma. The conventional treatment for certain cancers, such as medulloblastoma, is radiation therapy. Thus, the methods of the invention contemplate the use of itraconazole with radiation therapy to decrease the dosage of radiation required and/or improve the efficacy of treatment compared to radiation alone.

Dosage and Mode of Administration

As described, these compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

It will be appreciated that, while certain of the compounds according to this invention (i.e., compounds listed in Table 1) are readily available and are approved for certain uses in humans and/or animals, the amount or dose of compound required to inhibit hedgehog pathway activity may differ from (e.g., be greated or less than) the amount of compound required to achieve a result according to the approved use(s) of the compound.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, doses of the compounds of this invention for a patient will range from about 0.0001 to about 100 mg per kilogram of body weight per day. In certain embodiments, the dosage is between about 1 mg/kg and about 500 mg/kg, more preferably between about 5 mg/kg and about 50 mg/kg.

If desired, the effective daily dose of the active compound may be administered as two, three, four, five, six or more sub-doses administered separately at appropriate intervals throughout the day, optionally, in unit dosage forms.

The patient receiving this treatment is any animal in need, including primates, in particular humans, and other mammals such as equines, cattle, swine and sheep; and poultry and pets in general. An animal in need, in preferred embodiments, is a subject suffering from or susceptible to a disorder of Hh signaling.

The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutic effects of the first administered one is not entirely disappeared when the subsequent is administered.

The dosage range for administration will require at least the amount required for convential antifungal therapy. Amounts will be adjusted by the physician as necessary.

Therapeutic Methods

Preferred compounds for use in the therapeutic methods of the invention produce at least about 10% to 15% decrease in Hh signaling in a Hh signaling assay (see, e.g., the Example herein) relative to Hh signaling measured in absence of the tested compound in such a standard assay, more preferably at least about a 20% or 25% decrease in Hh signaling relative to a control, and still more preferably induce at least about 20%, 30%, 40%, 50%, 60%, 70%, 80%, 90% or 100% decrease in Hh signaling relative to absence of the tested compound in such a standard assay.

The methods of the present invention include inhibiting hedgehog pathway activity in a subject through the use of an inhibitory compound or pharmaceutical compositions comprising an effective amount of itraconazole administered to the subject, to thereby modulate hedgehog signaling. In exemplary embodiments, the inhibitory compound is itraconazole. The methods of the invention can be used in the regulation of malignant growth of a wide range of cells, tissues and organs, including normal cells, tissues, and organs, as well as those having the phenotype of ptc loss-of function, hedgehog gain-of-function, or smoothened gain-of-function. For instance, the subject method has therapeutic and cosmetic applications ranging from regulation of tumorigenesis, metastasis, neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Moreover, the subject methods can be performed on cells that are provided in culture (in vitro), or on cells in a whole animal (in vivo).

This method can be used to treat any disorder involving inappropriate or aberrant Hedgehog pathway activity. In preferred embodiments, the method can be used to treat cancer, arising in epithelia of endodermally-derived organs including small cell lung cancer, and carcinomas of the esophagus, stomach, pancreas, biliary tract, prostate, and bladder. Other indications appropriate for treatment by this method include basal cell carcinoma, medulloblastoma, rhabdomyosarcoma, ovarian cancer and multiple myeloma. In other embodiments, this invention may find application in the treatment of other conditions such as psoriasis and hirsutism.

The subject method can be used in the treatment of cancer. For instance, the subject compounds and composition can be used to treat prostate cancer, or metastatic prostate cancer. One exemplary use of the methods of the invention is in a population patients with aggressive, Hh-pathway-dependent prostate cancers. The compounds and methods of the invention can be used in these identified high-grade patients who refuse surgery.

In still another embodiment, the subject method can be used in the treatment of human cancers, particularly basal cell carcinomas and other tumors of epithelial tissues such as the skin. For example, subject compounds can be employed, in the subject method, as part of a treatment for basal cell nevus syndrome (BCNS), and other human carcinomas, adenocarcinomas, sarcomas and the like.

The method can be used in the treatment of neoplastic or hyperplastic transformations such as may occur in the central nervous system. For instance, the subject compounds can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In a preferred embodiment, the subject method is used as part of a treatment regimen for treating basal cell carcinoma. The deregulation of the hedgehog signaling pathway may be a general feature of basal cell carcinomas caused by ptc mutations. Consistent overexpression of human ptc mRNA has been described in tumors of familial and sporadic BCCs, determined by in situ hybridization. Mutations that inactivate ptc may be expected to result in overexpression of mutant Ptc, because ptc displays negative autoregulation. Prior research demonstrates that overexpression of hedgehog proteins can also lead to tumorigenesis. That sonic hedgehog (Shh) has a role in tumorigenesis in the mouse has been suggested by research in which transgenic mice overexpressing Shh in the skin developed features of BCNS, including multiple BCC-like epidermal proliferations over the entire skin surface, after only a few days of skin development. A mutation in the Shh human gene from a BCC was also described; it was suggested that Shh or other Hh genes in humans could act as dominant oncogenes in humans. Sporadic ptc mutations have also been observed in BCCs from otherwise normal individuals, some of which are UV-signature mutations. In one recent study of sporadic BCCs, five UV-signature type mutations, either CT or CCTT changes, were found out of fifteen tumors determined to contain ptc mutations. Another recent analysis of sporadic ptc mutations in BCCs and neuroectodermal tumors revealed one CT change in one of three ptc mutations found in the BCCs. See, for example, Goodrich et al. (1997) Science 277:1109-13; Xie et al. (1997) Cancer Res 57:2369-72; Oro et al. (1997) Science 276:817-21; Xie et al. (1997) Genes Chromosomes Cancer 18:305-9; Stone et al. (1996) Nature 384:129-34; and Johnson et al. (1996) Science 272:1668-71.

The subject method can also be used to treat patients with BCNS, e.g., to prevent BCC or other effects of the disease which may be the result of ptc loss-of-function, hedgehog gain-of-function, or smoothened gain-of-function. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyl, syndactyl, and spina bifida. They also develop a number of tumor types in addition to BCCs: fibromas of the ovaries and heart, cysts of the skin and jaws, and in the central nervous system, medulloblastomas and meningiomas. The subject method can be used to prevent or treat such tumor types in BCNS and non-BCNS patients. Studies of BCNS patients show that they have both genomic and sporadic mutations in the ptc gene, suggesting that these mutations are the ultimate cause of this disease.

In another aspect, the present invention provides pharmaceutical preparations and methods for controlling the formation of megakaryocyte-derived cells and/or controlling the functional performance of megakaryocyte-derived cells. For instance, certain of the compositions disclosed herein may be applied to the treatment or prevention of a variety hyperplastic or neoplastic conditions affecting platelets.

Another aspect of the present invention relates to a method of modulating a differentiated state, survival, and/or proliferation of a cell, such as a normal cell or a cell having a ptc loss-of-function, hedgehog gain-of-function, or smoothened gain-of-function, by contacting the cells with a compound as set forth above according to the subject method and as the circumstances may warrant.

For instance, because hedgehog, ptc, and smoothened appear to be involved in the formation of ordered spatial arrangements of differentiated tissues in vertebrates, the subject method could be used as part of a process for generating and/or maintaining an array of different, vertebrate tissue both in vitro and in vivo. The compound, whether inductive or anti-inductive with respect proliferation or differentiation of a given tissue, can be, as appropriate, any of the preparations described herein.

The invention also provides methods of inhibiting hedgehog signaling activity in a cell. The method includes the step of contacting the cell with (e.g., administering to the cell) an effective amount of any one of the compounds in Table 1, or a pharmaceutically acceptable salt thereof, thereby inhibiting hedgehog signaling activity in the cell.

In certain embodiments, the cell is not a neoplastic cell.

In another aspect, the invention provides a method of inhibiting hedgehog pathway activity in a cell. The method includes the step of administering an effective amount of a compound selected from the compounds of Table 1, or a pharmaceutically acceptable salt thereof, to the cell (contacting the cell with the compound), thereby inhibiting hedgehog pathway activity in the cell.

In certain embodiments of the above aspects, the cell is a mammalian cell, more preferably a human cell.

For example, the present methods of using subject compounds are applicable to cell culture techniques wherein it is desirable to control the proliferation or differentiation of the cell. A subject compound may be employed in a method directed towards cells which have a ptc loss-of-function, hedgehog gain-of-function, or smoothened gain-of-function phenotype. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such cultures for the generation of new neurons and glia. In such embodiments of the subject method, the cultured cells can be contacted with a compound of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motoneurons. Such neuronal cultures can be used as convenient assay systems as well as sources of implantable cells for therapeutic treatments.

The method of using subject compounds is applicable to cell culture techniques wherein it is desirable to control the proliferation or differentiation of the cell. A subject compound may be employed in a method directed towards cells which have a ptc loss-of-function, hedgehog gain-of-function, or smoothened gain-of-function phenotype that causes aberrant Hh signaling. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). GLOBAL: I am not entirely comfortable with the language "ptc loss-of-function, hedgehog gain-of-function, or smoothened gain-of-function phenotype" referring to target genes, pathway activation will mean all these above things.

Yet another aspect of the present invention concerns the observation in the art that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising one or more of the subject compounds can also be utilized for both cell culture and therapeutic methods involving generation and maintenance of tissue.

Levine et al. (1997) J Neurosci 17:6277 show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) Development 124:363 demonstrated that treatment of cultures of perinatal mouse retinal cells with the amino-terminal fragment of Sonic hedgehog results in an increase in the proportion of cells that incorporate bromodeoxyuridine, in total cell numbers, and in rod photoreceptors, amacrine cells and Muller glial cells, suggesting that Sonic hedgehog promotes the proliferation of retinal precursor cells. Thus, the subject method can be used in the treatment of proliferative diseases of retinal cells and regulate photoreceptor differentiation.

The present invention can be used to control hair growth. Hair is basically composed of keratin, a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

The subject method can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, subject compounds can be used to manage hirsutism, a disorder marked by abnormal hairiness. The subject method can also provide a process for extending the duration of depilation.

Moreover, because a subject compound will often be cytostatic to epithelial cells, rather than cytotoxic, such agents can be used to protect hair follicle cells from cytotoxic agents which require progression into S-phase of the cell-cycle for efficacy, e.g. radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, subject compounds can be used for patients undergoing chemo- or radiation-therapies which ordinarily result in hair loss. By inhibiting cell-cycle progression during such therapies, the subject treatment can protect hair follicle cells from death which might otherwise result from activation of cell death programs. After the therapy has concluded, the instant method can also be removed with concommitant relief of the inhibition of follicle cell proliferation.

The subject method of inhibiting Hh signaling activity can also be used in the treatment of folliculitis, such as folliculitis decalvans, folliculitis ulerythematosa reticulata or keloid folliculitis. For example, a cosmetic preparation of a subject compound can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, the subject method of inhibiting Hh signaling can be used to induce differentiation and/or inhibit proliferation of epithelial tissue derivatives. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin: the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of a subject compound, e.g., which promotes quiescense or differentiation, can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with an antiproliferative embodiment of the subject method can be used to reverse the pathological epidermal activation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a subject compound composition in amounts sufficient to inhibit hyperproliferation of epidermal/epidermoid cells of the lesion.

Acne represents yet another dermatologic ailment which may be treated by the subject method. Acne vulgaris, for instance, is a multifactorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by Propinobacterium acnes and *Staphylococcus* epidemmidis bacteria and Pitrosporum ovale, a yeast. Treatment with an antiproliferative subject compound, particularly topical preparations, may be useful for preventing the transitional features of the ducts, e.g. hypercornification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions which are either pruritic, erythematous, scaly, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that is due to exposure to actinic radiation such as that from the sun, ultraviolet waves or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipruritics, and antibiotics.

Ailments which may be treated by the subject method are disorders specific to non-humans, such as mange.

Ptc, hedgehog, and smoothened are apparently involved in controlling the development of stem cells responsible for formation of the digestive tract, liver, lungs, and other organs which derive from the primitive gut Shh serves as an inductive signal from the endoderm to the mesoderm, which is critical to gut morphogenesis. Therefore, for example, compounds of the instant method can be employed for regulating the development and maintenance of an artificial liver which can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

Methods of Monitoring

In certain embodiments of the method, prostate specific antigen (PSA) levels are monitored. PSA screening is currently the single best test for prostate cancer, although some men with prostate cancer may have normal PSA levels. PSA is an excellent marker for the follow-up of patients with established prostate cancer.

PSA is a single-chain glycoprotein with molecular weight of 34,000 Da. It is produced in prostatic ductal epithelium, secreted into the prostatic ducts, and then concentrated in the seminal plasma. In serum, PSA reaches the circulation by diffusing through the prostatic stroma.

Serum PSA levels increase with age. The traditional upper limit of reference range levels of PSA is 4 ng/mL, but age-specific PSA reference range levels devised by Oesterling et al can be used. Age-related PSA reference range levels are as follows:

Patients aged 40-49 years, 0-2.5 ng/mL
Patients aged 50-59 years, 0-3.5 ng/mL
Patients aged 60-69 years, 0-4.5 ng/mL
Patients aged 70-79 years, 0-6.5 ng/mL PSA is produced by both abnormal and normal prostate tissue. A moderate elevation of the PSA level (4-10 ng/mL) has a low specificity for prostate cancer. Some men with prostate cancer have PSA levels in the reference range. An elevated PSA level is not specific for prostate cancer, and elevated serum PSA levels may also be associated with prostatitis, prostate infarction, PIN, prostate biopsy, transurethral resection of the prostate, and urethral catheterization.

Kits or Pharmaceutical Systems

The present compounds and compositions may be assembled into kits or pharmaceutical systems for use in treatment of conditions requiring inhibition of hedgehog pathway activity. Kits or pharmaceutical systems according to this aspect of the invention include a hedgehog antagonist compound according to this invention (e.g., a compound of Table 1, such as itraconazole), preferably in unit dosage form. The compound may be present together with a pharmaceutically acceptable solvent, carrier, excipient, or the like, as described herein.

The kits or pharmaceutical systems of the invention may also include associated instructions for using the compounds of the invention for treating conditions related to abnormal or aberrant hedgehog pathway activity. The instructions will generally include information about the use of the compound for treatment of a disease or disorder or symptoms thereof associated with angiogenesis; in preferred embodiments, the instructions include at least one of the following: description of the angiogenesis-inhibiting compound; dosage schedule and administration for treatment of a disease or disorder or symptoms thereof associated with abnormal or aberrant hedgehog pathway activity; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The kit may also include one or more container means, such as vials, tubes, ampules, bottles and the like, for containing the compound (and optionally carried within a carrier means, such as a box, carton, tube or the like). Such containers can be made of plastic, glass, laminated paper, metal foil, or other materials suitable for holding medicaments.

EXAMPLES

Example 1

Itraconazole Treatment in Prostate Cancer Models

Evidence for a critical role of continuous Hh pathway activity in cancer growth comes from the ability of cyclopamine, a potent antagonist of the Hedgehog (Hh) signaling pathway [4,7,13] to inhibit cancer growth in animal models of malignancies arising in tissues such as lung, pancreas, bilary tract, prostate, skin, and brain [2,3,9,15,17].

A library of drugs was previously tested in humans for agents that antagonize Hedgehog signaling. This library currently contains ~2400 compounds that have gone at least as far as Phase II testing in human trials, and includes many FDA-approved drugs, and is several fold larger than any other such known library available to academic researchers (see, e.g, PCT Publication No. WO2006/004795, incorporated herein by reference). In previous work a library of 40,000 synthetic small molecules was assembled and screened, and about fifteen families of compounds with submicromolar potencies in Hh pathway inhibition were identified [5]. The assays used for the screen for Hh pathway antagonists proceeded essentially as described in reference 5. Briefly, each candidate compound was added at 10 uM to a cultured cell based Sonic hedgehog (Shh) signaling assay in high throughput format. This assay utilized cells with a stably integrated firefly luciferase reporter that is responsive to ShhN signaling. These cells also contain a stably integrated, constitutively expressed Renila luciferase gene that can be used for normalization of response to Shh, and used also to monitor cell health. Levels of Renila luciferase vary slightly, a few of the drugs in the library are cytotoxic, however most drugs do not significantly affect cell health. Once the initial 10 uM hits were identified, additional titrations of candidate drugs were carried out to determine their $IC_{50}$ values in pathway inhibition. Table 1, below, shows a list of these hits and their $IC_{50}$ value

| Number | Drug name | IC50 | FDA approved? |
|---|---|---|---|
| 1 | SALINOMYCIN, SODIUM<br>ex *Streptomyces albus*<br>J Antibiotics 27: 814 (1954) | <0.1 uM | |
| 2 | OLIGOMYCIN (A shown)<br>Therap cat: antibiotic, antifungal | <0.1 uM | |
| 3 | Colchicine | <0.1 uM | Y |
| 4 | Podophyllum resin | <0.1 uM | Y |
| 5 | Anisomycin | <0.1 uM | Y |
| 6 | Croton oil | <0.1 uM | Y |
| 7 | Ipecac syrup | <0.1 uM | Y |
| 8 | Vindesine | <0.1 uM | INN, BAN |
| 9 | Vincristine sulfate | <0.1 uM | Y |
| 10 | Demecolcine | <0.1 uM | INN; BAN; DCF; MI. |
| 11 | Vinorelbine tartrate | <0.1 uM | Y |
| 12 | LOXAPINE SUCCINATE<br>Therap cat: antipsychotic | 0.1 uM~0.3 uM | |
| 13 | Cyproheptadine | 0.1 uM~0.3 uM | Y |
| 14 | Itraconazole | 0.3 uM | Y |
| 15 | COLCHICEINE<br>antimitotic ex *Colchicum autumnale*<br>Col Czech Chem Commun 19: 805 (1954) | 0.3 uM~1 uM | |
| 16 | PIMETHIXENE MALEATE<br>Therap cat: H1-antihistamine | 0.3 uM~1 uM | |
| 17 | Diaziquone | 0.3 uM~1 uM | INN |
| 18 | Sulfisomidine | 0.3 uM~1 uM | Y |
| 19 | Cycloheximide | 0.3 uM~1 uM | INN |
| 20 | Cyclopamine | 0.3 uM~1 uM | N |
| 21 | Cod liver oil | 0.3 uM~1 uM close to 0.3 uM | Y |
| 22 | METHOXYVONE<br>Therap cat: anabolic | 0.3 uM~1 uM close to 1 uM | |
| 23 | PROMETHAZINE HYDROCHLORIDE<br>Therap cat: antihistaminic | 0.3 uM~1 uM close to 1 uM | |
| 24 | SULFAQUINOXALINE SODIUM<br>Therap cat: antibacterial | 0.3 uM~1 uM close to 1 uM | |
| 25 | Vinblastine sulfate AND 1545 | 0.3 uM~1 uM close to 1 uM | Y |
| 26 | Hydroxyzine | 0.3 uM~1 uM close to 1 uM | Y |
| 27 | Eucalyptol (Cineole) | 0.3 uM~1 uM close to 1 uM | Y |
| 28 | ROTENONE<br>Therap cat: acaricide, ectoparasiticide<br>inhibits NADH2 oxidation to NAD | 1 uM~3 uM | |
| 29 | PHENOXYBENZAMINE HYDROCHLORIDE<br>Therap cat: alpha adrenergic blocker | 1 uM~3 uM | |
| 30 | 5-AZACYTIDINE<br>Therap cat: Antineoplastic<br>pyrimidine antimetabolite: inhibits nucleic acid<br>Replication | 1 uM~3 uM | |
| 31 | W-7 HYDROCHLORIDE<br>Therap cat: calmodulin antagonist | 1 uM~3 uM | |
| 32 | DIHYDROARTEMISIMIN<br>Therap cat: antimalarial, anti-inflammatory<br>Med Res Rev 7: 29 (1987) | 1 uM~3 uM | |
| 33 | Clomipramine | 1 uM~3 uM | Y |
| 34 | Raloxifene hydrochloride | 1 uM~3 uM | Y |
| 35 | Doxazosin mesylate salt | 1 uM~3 uM | Y |
| 36 | Chloroquine diphosphate salt | 1 uM~3 uM | Y |
| 37 | Imipramine | 1 uM~3 uM | Y |
| 38 | Thioridazine | 1 uM~3 uM | Y |
| 39 | Clothiapine | 1 uM~3 uM | INN, BAN, JAN |
| 40 | Zolantidine | 1 uM~3 uM | N |
| 41 | CRASSIN ACETATE<br>antiviral, constituent of numerous gorgonids;<br>mp 123-125<br>Rec Trav Chem 88: 1413 | 1 uM~3 uM close to 1 uM | |
| 42 | ESTRIOL BENZYL ETHER<br>Therap cat: estrogen | 1 uM~3 uM close to 1 uM | |
| 43 | | 1 uM~3 uM close to 1 uM | |
| 44 | Manganese chloride | 1 uM~3 uM close to 1 uM | Y |
| 45 | Fluphenazine N-mustard (SKF-7171A) | 1 uM~3 uM close to 1 uM | ANALOG |
| 46 | Almond oil | 1 uM~3 uM close to 1 uM | Y |

-continued

| Number | Drug name | IC50 | FDA approved? |
|---|---|---|---|
| 47 | PROMAZINE HYDROCHLORIDE Therap cat: antipsychotic | 1 uM~3 uM close to 3 uM | |
| 48 | ESTRADIOL ACETATE Therap cat: estrogen | 1 uM~3 uM close to 3 uM | |
| 49 | TRIMIPRAMINE MALEATE Therap cat: antidepressant | 1 uM~3 uM close to 3 uM | |
| 50 | _-Estradiol 3-benzoate | 1 uM~3 uM close to 3 uM | Y |
| 51 | Copper (II) acetate | 1 uM~3 uM close to 3 uM | |
| 52 | Amitriptyline | 1 uM~3 uM close to 3 uM | Y |
| 53 | Chlorquinaldol(5,7-Dichloro-2-methyl-8-quinolinol) | 3 uM | Y |

As shown in FIG. 1A, itraconazole treatment at two doses (25 and 37.5 mg/kg) was as effective as cyclopamine in extending survival in the AT6.3 Dunning model throughout the month-long experimental period, whereas control-treated mice died in approximately 2 weeks. Itraconazole treatment at 37.5 mg/kg similarly was as effective as cyclopamine in causing a complete and durable regression of the 22RV1 xenografts, whereas the lower dose (25 mg/kg) only slowed tumor growth in comparison to control treatment (FIG. 1B). Thus, it is possible that itraconazole and other pharmaceutical agents which interfere with Hedgehog signal transduction activity of hedgehog, ptc, smoothened, or other pathway components will likewise be capable of inhibiting proliferation (or other biological consequences) in normal cells and/or cells having a patched loss-of-function phenotype, a hedgehog gain-of-function phenotype, or a smoothened gain-of-function phenotype.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

References

1. Beachy, P. A., Karhadkar, S. S. & Berman, D. M. (2004). Tissue repair and stem cell renewal in carcinogenesis. *Nature* 432, 324-31.
2. Berman, D. M., Karhadkar, S. S., Hallahan, A. R., Pritchard, J. I., Eberhart, C. G., Watkins, D. N., Chen, J. K., Cooper, M. K., Taipale, J., Olson, J. M. & Beachy, P. A. (2002). Medulloblastoma growth inhibition by hedgehog pathway blockade. *Science* 297, 1559-61.
3. Berman, D. M., Karhadkar, S. S., Maitra, A., Montes De Oca, R., Gerstenblith, M. R., Briggs, K., Parker, A. R., Shimada, Y., Eshleman, J. R., Watkins, D. N. & Beachy, P. A. (2003). Widespread requirement for Hedgehog ligand stimulation in growth of digestive tract tumours. *Nature* 425, 846-51.
4. Chen, J. K., Taipale, J., Cooper, M. K. & Beachy, P. A. (2002). Inhibition of Hedgehog signaling by direct binding of cyclopamine to Smoothened. *Genes Dev* 16, 2743-8.
5. Chen, J. K., Taipale, J., Young, K. E., Maiti, T. & Beachy, P. A. (2002). Small molecule modulation of Smoothened activity. *Proc Natl Acad Sci USA* 99, 14071-6.
6. Cherny, R. A., Atwood, C. S., Xilinas, M. E., Gray, D. N., Jones, W. D., McLean, C. A., Barnham, K. J., Volitakis, I., Fraser, F. W., Kim, Y., Huang, X., Goldstein, L. E., Moir, R. D., Lim, J. T. et al. (2001). Treatment with a copper-zinc chelator markedly and rapidly inhibits beta-amyloid accumulation in Alzheimer's disease transgenic mice. *Neuron* 30, 665-76.
7. Cooper, M. K., Porter, J. A., Young, K. E. & Beachy, P. A. (1998). Plant-derived and synthetic teratogens inhibit the ability of target tissues to respond to Sonic hedgehog signaling. *Science* 280, 1603-1607.
8. Fan, L., Pepicelli, C. V., Dibble, C. C., Catbagan, W., Zarycki, J. L., Laciak, R., Gipp, J., Shaw, A., Lamm, M. L., Munoz, A., Lipinski, R., Thrasher, J. B. & Bushman, W. (2004). Hedgehog signaling promotes prostate xenograft tumor growth. *Endocrinology* 145, 3961-70.
9. Karhadkar, S. S., Bova, G. S., Abdallah, N., Dhara, S., Gardner, D., Maitra, A., Isaacs, J. T., Berman, D. M. & Beachy, P. A. (2004). Hedgehog signaling in prostate regeneration, neoplasia and metastasis. *Nature* 431, 707-12.
10. Romer, J. T., Kimura, H., Magdaleno, S., Sasai, K., Fuller, C., Baines, H., Connelly, M., Stewart, C. F., Gould, S., Rubin, L. L. & Curran, T. (2004). Suppression of the Shh pathway using a small molecule inhibitor eliminates medulloblastoma in Ptcl+/−p53−/− mice. *Cancer Cell* 6, 229-240.
11. Sanchez, P., Hernandez, A. M., Stecca, B., Kahler, A. J., DeGueme, A. M., Barrett, A., Beyna, M., Datta, M. W., Datta, S. & Ruiz i Altaba, A. (2004). Inhibition of prostate cancer proliferation by interference with SONIC HEDGEHOG-GLI1 signaling. *Proc Natl Acad Sci USA* 101, 12561-6.
12. Sheng, T., Li, C., Zhang, X., Chi, S., He, N., Chen, K., McCormick, F., Gatalica, Z. & Xie, J. (2004). Activation of the hedgehog pathway in advanced prostate cancer. *Mol Cancer* 3, 29.
13. Taipale, J., Chen, J. K., Cooper, M. K., Wang, B., Mann, R. K., Milenkovic, L., Scott, M. P. & Beachy, P. A. (2000).

Effects of oncogenic mutations in Smoothened and Patched can be reversed by cyclopamine. *Nature* 406, 1005-9.
14. Taipale, J. & Beachy, P. A. (2001). The Hedgehog and Wnt signaling pathways in cancer. *Nature* 411, 349-54.
15. Thayer, S. P., Di Magliano, M. P., Heiser, P. W., Nielsen, C. M., Roberts, D. J., Lauwers, G. Y., Qi, Y. P., Gysin, S., Fernandez-Del Castillo, C., Yajnik, V., Antoniu, B., McMahon, M., Warshaw, A. L. & Hebrok, M. (2003). Hedgehog is an early and late mediator of pancreatic cancer tumorigenesis. *Nature* 425, 851-6.
16. Tiffert, T., Ginsburg, H., Krugliak, M., Elford, B. C. & Lew, V. L. (2000). Potent antimalarial activity of clotrimazole in in vitro cultures of *Plasmodium falciparum*. *Proc Natl Acad Sci USA* 97, 331-6.
17. Watkins, D. N., Berman, D. M., Burkholder, S. G., Wang, B., Beachy, P. A. & Baylin, S. B. (2003). Hedgehog signaling within airway epithelial progenitors and in small-cell lung cancer. *Nature* 422, 313-7.
18. Williams, J. A., Guicherit, 0. M., Zaharian, B. I., Xu, Y., Chai, L., Wichterle, H., Kon, C., Gatchalian, C., Porter, J. A., Rubin, L. L. & Wang, F. Y. (2003). Identification of a small molecule inhibitor of the hedgehog signaling pathway: Effects on basal cell carcinoma-like lesions. *Proc Natl Acad Sci USA* 100, 4616-21.
19. Zhu, S., Stavrovskaya, I. G., Drozda, M., Kim, B. Y., Ona, V., Li, M., Sarang, S., Liu, A. S., Hartley, D. M., Wu du, C., Gullans, S., Ferrante, R. J., Przedborski, S., Kristal, B. S. et al. (2002). Minocycline inhibits cytochrome c release and delays progression of amyotrophic lateral sclerosis in mice. *Nature* 417, 74-8.
20. Dahmane et al. (1997) *Nature* 389(6653):876-881.
21. Mann R K and Beachy P A. (2004) *Ann Rev Biochem* (73): 891-923.
22. Cooper M K, Wassif C A, Krakowiak P A, Taipale J, Gong R, Kelley R I, Porter F D, Beachy P A. (2003) *Nature Genetics*. 33: 508-513.

What is claimed is:

1. A method of treating cancer in a subject having cancer, comprising administering parenterally a therapeutically effective amount of itraconazole, or a pharmaceutically acceptable salt thereof, to the subject, wherein the cancer is selected from prostate cancer, metastatic prostate cancer, small cell lung cancer, non-small cell lung cancer, carcinomas of the esophagus, stomach, pancreas, biliary tract, prostate, bladder, basal cell carcinoma, melanoma, squamous cell carcinoma, medulloblastoma, rhabdomyosarcoma, breast cancer, or ovarian cancer, thereby treating the cancer.

2. The method of claim 1, wherein the cancer is prostate cancer.

3. The method of claim 1, wherein the cancer is basal cell or squamous cell carcinoma.

4. The method of claim 1, wherein the cancer is melanoma.

5. The method of claim 1, wherein the administering is intraperitoneal or intravenous.

6. The method of claim 2, wherein the prostate cancer is metastatic prostate cancer.

7. The method of claim 1, wherein the cancer is characterized by Hedgehog (Hh) pathway activation.

8. The method of claim 1, wherein the melanoma is metastatic.

9. The method of claim 1, further comprising co-administering at least one chemotherapeutic agent.

10. A method of treating skin cancer in a subject having skin cancer, comprising administering a therapeutically effective amount of topical composition consisting essentially of itraconazole, or a pharmaceutically acceptable salt thereof, to the subject, thereby treating the skin cancer.

11. The method of claim 10, wherein the cancer is selected from basal cell carcinoma, melanoma, or squamous cell carcinoma.

12. The method of claim 10, further comprising co-administering at least one chemotherapeutic agent.

13. A method of treating cancer in a subject having cancer, comprising administering orally a therapeutically effective amount of itraconazole, or a pharmaceutically acceptable salt thereof, to the subject, wherein the cancer is selected from prostate cancer, metastatic prostate cancer, small cell lung cancer, non-small cell lung cancer, carcinomas of the esophagus, stomach, pancreas, biliary tract, prostate, or bladder, basal cell carcinoma, melanoma, squamous cell carcinoma, medulloblastoma, rhabdomyosarcoma, breast cancer, or ovarian cancer, thereby treating the cancer.

14. A kit comprising itraconazole in unit dosage form, together with instructions for using itraconazole parenterally or orally for treating cancer, wherein the cancer is selected from prostate cancer, metastatic prostate cancer, small cell lung cancer, non-small cell lung cancer, carcinomas of the esophagus, stomach, pancreas, biliary tract, prostate, bladder, basal cell carcinoma, melanoma, squamous cell carcinoma, medulloblastoma, rhabdomyosarcoma, breast cancer, or ovarian cancer.

15. The kit of claim 14, wherein the administering is oral, intraperitoneal, or intravenous.

16. A kit comprising a composition consisting essentially of itraconazole in unit dosage form, together with instructions for using itraconazole topically for treating skin cancer.

17. The kit of claim 16, wherein the cancer is selected from basal cell carcinoma, melanoma, or squamous cell carcinoma.

* * * * *